(12) United States Patent
Chamberlain et al.

(10) Patent No.: US 9,028,465 B2
(45) Date of Patent: May 12, 2015

(54) THERAPEUTIC DELIVERY DEVICES, SYSTEMS, AND METHODS

(71) Applicant: Grifols, S.A., Barcelona (ES)

(72) Inventors: Dean Chamberlain, Cary, NC (US);
Valery Novokhatny, Raleigh, NC (US);
David Fineberg, Raleigh, NC (US)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 13/859,395

(22) Filed: Apr. 9, 2013

(65) Prior Publication Data
US 2013/0289528 A1    Oct. 31, 2013

Related U.S. Application Data

(63) Continuation of application No. 13/581,697, filed as application No. PCT/US2011/026938 on Mar. 3, 2011, now Pat. No. 8,840,637.

(60) Provisional application No. 61/310,558, filed on Mar. 4, 2010.

(51) Int. Cl.
*A61M 25/10*    (2013.01)
*A61B 17/12*    (2006.01)
*A61M 25/00*    (2006.01)

(52) U.S. Cl.
CPC .......... *A61M 25/104* (2013.01); *A61B 17/1204* (2013.01); *A61B 17/12109* (2013.01); *A61B 17/12136* (2013.01); *A61B 17/12172* (2013.01); *A61M 25/00* (2013.01); *A61M 25/0026* (2013.01); *A61M 25/10* (2013.01); *A61M 2025/0004* (2013.01);

(Continued)

(58) Field of Classification Search
CPC ............ A61M 25/10; A61M 25/1011; A61M 25/104; A61M 2025/105; A61M 2025/1052; A61M 2025/1061; A61M 2025/1079; A61M 2025/1081
USPC .............. 604/103.05, 101.04, 96.01; 606/200
See application file for complete search history.

(56) References Cited

U.S. PATENT DOCUMENTS

| | | |
|---|---|---|
| 4,689,041 A | 8/1987 | Corday et al. |
| 5,279,546 A | 1/1994 | Mische et al. |
| 5,637,086 A | 6/1997 | Ferguson et al. |

(Continued)

FOREIGN PATENT DOCUMENTS

| | | |
|---|---|---|
| WO | WO 9711738 | 4/1997 |
| WO | WO 2006019728 | 2/2006 |

OTHER PUBLICATIONS

Sato et al., Serum cardiac troponin T and plasma brain natriuretic peptide in patients with cardiac decompensation, Heart 88:647-648 (2002).

(Continued)

*Primary Examiner* — Laura Bouchelle
(74) *Attorney, Agent, or Firm* — Womble Carlyle Sandridge & Rice, LLP; Carl B. Massey, Jr.; Bernard A. Brown, II

(57) ABSTRACT

Devices, systems, and methods for delivery of therapeutics, in particular thrombolytic agents, in particular plasmin, are provided. The devices, systems, and methods also provide for occlusion of a vessel or graft distal and/or proximal to a treatment zone. Also provided are devices, systems, and methods that trap emboli.

15 Claims, 8 Drawing Sheets

(52) U.S. Cl.
CPC . *A61M 2025/105* (2013.01); *A61M 2025/1052* (2013.01); *A61M 2025/1097* (2013.01)

(56) References Cited

U.S. PATENT DOCUMENTS

| | | | |
|---|---|---|---|
| 5,925,016 A * | 7/1999 | Chornenky et al. | 604/96.01 |
| 6,485,500 B1 | 11/2002 | Kokish et al. | |
| 6,488,672 B1 | 12/2002 | Dance et al. | |
| 6,533,767 B2 * | 3/2003 | Johansson et al. | 604/507 |
| 6,547,754 B1 | 4/2003 | Evans et al. | |
| 6,958,059 B2 | 10/2005 | Zadno-Azizi | |
| 7,141,045 B2 | 11/2006 | Johansson et al. | |
| 7,763,010 B2 | 7/2010 | Evans et al. | |
| 2001/0031981 A1 | 10/2001 | Evans et al. | |
| 2005/0107738 A1 | 5/2005 | Slater et al. | |

OTHER PUBLICATIONS

Working Party on Thrombolysis in the Management of Limb Ischemia, Thrombolysis in the Management of Lower Limb Peripheral . . . , J. Vasc. Interv. Radiol.7: S337-S349 (2003).

* cited by examiner

THERAPEUTIC DELIVERY DEVICES, SYSTEMS, AND METHODS

CROSS-REFERENCE TO RELATED APPLICATIONS

This application is a continuation of U.S. patent application Ser. No. 13/581,697, filed Aug. 29, 2012, and having a 35 U.S.C. §371(c) date of Nov. 12, 2012, which is a national phase application under 35 U.S.C. §371 of International Application Serial No. PCT/US11/26938, filed Mar. 3, 2011, that claims benefit of priority under 35 U.S.C. §119 to U.S. Provisional Application No. 61/310,558, filed Mar. 4, 2010, the contents of each which are hereby incorporated by reference in their entirety.

FIELD OF THE INVENTION

The present invention relates to devices, systems, and methods for delivery of therapeutics, in particular thrombolytic agents, wherein the devices, systems, and methods provide for occlusion of a vessel or graft distal and/or proximal to a treatment zone.

BACKGROUND OF THE INVENTION

The current standard of care for use of thrombolytic in clinical treatment of acute peripheral arterial occlusion (aPAO) is intrathrombus administration of tissue plasminogen activator (t-PA). In approximately 20% of patients administered t-PA via intrathrombus delivery, dissolution of clot is heralded by temporary worsening of the lower leg ischemia prior to improvement. This temporary worsening corresponds to fragmentation of the clot and showering of emboli into distal circulation. Over the next 6-12 hours, the systemic activity of t-PA is known to slowly dissolve these clots, after which symptoms of worsening ischemia generally abate. The condition of the patient subsequently improves slowly to ameliorate the aPAO symptoms that represent native artery or graft occlusion.

One of the safety advantages of a thrombolytic agent such as plasmin is its ability to be neutralized rapidly in the blood by circulating inhibitors. However, there is evidence to suggest that the flow dynamics of a treatment zone can be such that plasmin may escape into the bloodstream prior to contacting its fibrin substrate on the clot and also that blood along with its contained inhibitors can enter the treatment zone during plasmin application and interfere with thrombolysis by inactivating the plasmin.

A need remains for thrombolytic agent delivery devices, systems, and methods that also provide for effective occlusion of a vessel or graft distal and/or proximal to an occlusion.

SUMMARY OF THE INVENTION

In one aspect, the present invention provides a coaxial infusion catheter system comprising:
(a) an occlusion catheter component; and
(b) an infusion catheter component, wherein at least a portion of the occlusion catheter is coaxially positioned within the infusion catheter, wherein the occlusion catheter provides for occlusion of a vessel or graft distal to an occlusion, wherein a composition comprising a thrombolytic agent can be infused into an annular fluid passageway between the outer wall of the occlusion catheter and the inner wall of the infusion catheter thereby providing the agent to a treatment zone.

In another aspect, the present invention provides an infusion catheter for delivering a thrombolytic agent to an occlusion in a vessel or graft, wherein the catheter comprises:
(a) an infusion zone; and
(b) an occlusion chamber disposed about an outer surface of its shaft about a region proximal to the infusion zone.

In some aspects, the present invention provides an infusion catheter for delivering a thrombolytic agent to an occlusion in a vessel or graft, wherein the catheter comprises:
(a) an infusion zone; and
(b) an occlusion chamber disposed about an outer surface of its shaft about a region distal to the infusion zone.

In other aspects, the present invention provides a coaxial infusion catheter system comprising:
(a) an infusion catheter component having a infusion zone for infusing a thrombolytic agent to an occlusion in a vessel or a graft; and
(b) an occluding catheter component having an elongate body, wherein an expandable occluding element is coupled to a distal end of the elongate body, wherein the element when expanded and in an open configuration is capable of occluding a vessel or graft distal to a treatment zone, wherein the element when expanded and in a closed position is capable of allowing blood flow through the treatment zone.

DETAILED DESCRIPTION

The devices, systems, and methods of the present invention can provide for delivery of a composition, preferably a solution, comprising any therapeutic. In the preferred embodiment, the therapeutic is a thrombolytic agent. Thrombolytic agents include, but are not limited to, plasmin and derivatives thereof. For example, plasmin and truncated variants thereof (e.g., plasmin, mini-plasmin, micro-plasmin, etc.) can be delivered to a treatment zone for contact with an occlusion (e.g., a clot) in a vessel (e.g., peripheral artery) or graft. In some embodiments, the system, devices, and methods of the present invention provide for acute peripheral arterial occlusion (aPAO) indications.

Figure 1:
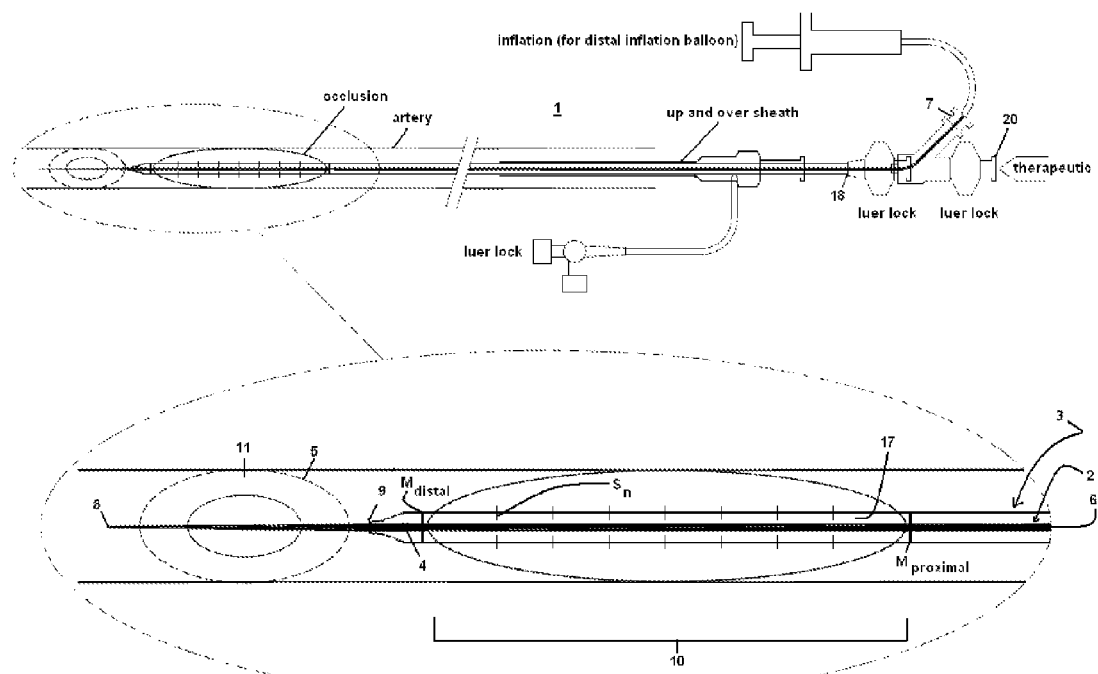
FIG. 1 is a schematic side view of one embodiment of a catheter system and its components in accordance with the present invention. An occlusion catheter component occludes a vessel or graft distal to an occlusion (e.g., a clot).

In one aspect, the present invention is based on a coaxial infusion catheter system 1 depicted in FIG. 1.

In one embodiment, the system comprises: a) an occlusion catheter 2 component; and b) an infusion catheter 3 component, wherein at least a portion of the occlusion catheter is coaxially positioned within the infusion catheter. Fluid can be infused into an annular fluid passageway between the outer wall of the occlusion catheter 2 and the inner wall of infusion catheter 3. For example, a syringe containing a thrombolytic agent can be used to inject a solution comprising the agent whereby the solution advances through the annular fluid passageway exiting through side port slits of the infusion catheter 3 into a vessel (e.g., artery), graft, and/or occlusion (e.g., thrombus).

Preferably, the system components are dimensioned such that an infusion zone is maximized and the device length outside the patient is minimized. In one embodiment, the infusion zone length corresponds to the subject's overall treatment zone (e.g., clot mass inside an artery) in order to ensure uniform drug delivery throughout the treatment zone. Preferably, the portion of the system external to the patient is kept as short as possible so as to at least avoid or minimize complications arising from patient movement during treatment.

Occlusion Catheter

In one embodiment, the occlusion catheter 2 of FIG. 1 comprises a tubular occlusion catheter shaft 4 and an inflatable occlusion chamber 5. In some embodiments, catheter 2 is made of nylon or other similar material. Preferably, the occlusion catheter 2 has a three French outer diameter with a central inflation lumen 6 that is continuous from the proximal tip end 7 to the distal tip end 8 thus providing a direct path from the proximal tip end 7 to the inflatable occlusion chamber 5. When assembled with the infusion catheter 3 as shown in FIG. 1, the distal tip 8 extends beyond the infusion catheter's distal tip 9 such that the inflatable occlusion chamber 5 also lies distal to the infusion catheter's distal tip 9 thereby capable of providing occlusion of a vessel or graft distal to the infusion zone 10. In some embodiments, the inflatable occlusion chamber 5 lies distal to the infusion catheter's distal tip 9 by at least about 0.1 cm, illustratively, by at least about: 0.1, 0.5, 1, and 2 centimeters.

In one embodiment, the inflatable occlusion chamber 5 is formed of a urethane polymer or a thermoplastic rubber elastomer. In another embodiment, the chamber 5 is a Latex balloon. The inflatable occlusion chamber 5 is expandable between a collapsed configuration and an inflated configuration. Upon inflation, the occlusion chamber conforms to the shape of the interior of the body lumen in which the system 1 is disposed, such as a blood vessel. In the collapsed configuration (not shown), the inflatable occlusion chamber 5 has the same general diameter (or less) as the distal end of the shaft 8.

In another embodiment, the occlusion chamber 5 can be sized as appropriate to substantially or completely occlude a particular vessel or graft in which the system will be used. In some embodiments, the occlusion catheter 2 has a length that is at least about 0.5 cm, illustratively, about 0.5 cm to about 2 cm. In another embodiment, the inflatable occlusion chamber 5 has a collapsed diameter of at most about 0.039 inches; and an expanded diameter up to about 1.5 cm.

The inflatable occlusion chamber 5 can be inflated to various diameters, depending on the volume of the material (e.g., air, gas, fluid) inserted into the inflatable occlusion chamber 5. In some embodiments, a single size occlusion catheter 2 is used. In order to facilitate inflation to a desired balloon diameter and avoid over-inflation, a chart can be provided listing various balloon diameters and the volume of inflation fluid generally required to achieve each diameter. In other embodiments, one or more occlusion catheter 2s are sequentially used with the infusion catheter, wherein the one or more occlusion catheter 2s are of different sizes and/or configurations relative to each other.

The inflatable occlusion chamber 5 can be inflated via inflation lumen 6, which is in communication with the interior of the inflatable occlusion chamber 5. When an inflation material (e.g., air, gas, fluid) is inserted through the inflation lumen 6 into the inflatable occlusion chamber 5, at least the intermediate portion 11 of the occlusion chamber 5 moves radially outward.

In one embodiment, the occlusion catheter 2 is a balloon catheter comprising an inflatable balloon (i.e., the inflatable occlusion chamber).

Figure 2:
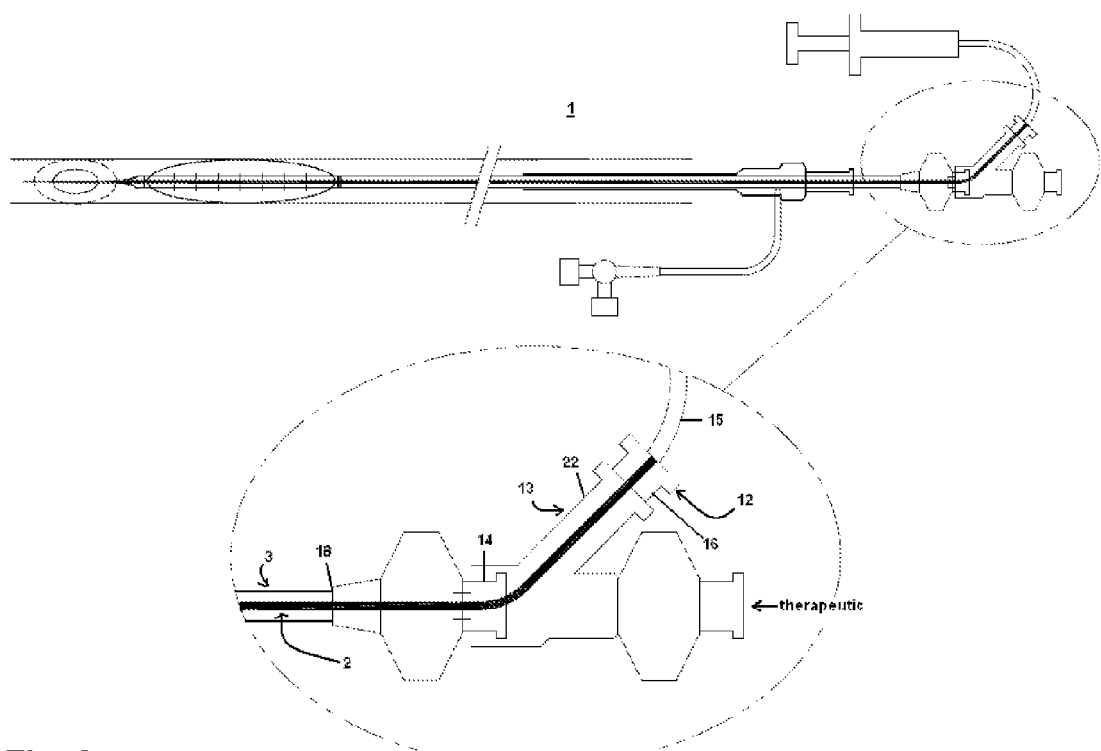
FIG. 2 is another schematic side view of the catheter system of FIG. 1.

Referring to FIG. 2, in some embodiments, a hub assembly provides for connecting an inflation source, directly or indirectly, to the inflation lumen 6. In the illustrated embodiment shown in FIG. 2, the occlusion catheter 2 further comprises an occlusion catheter hub 12. In some embodiments, the hub 12 comprises a rotating male luer thread collar (not shown). The hub can be made of plastic, for example. When the system 1 is assembled, the rotating male luer thread collar engages a hub connector assembly 13, which is engaged with hub 14 of the infusion catheter, to provide communication between the inflation source 15 and the inflation lumen 6 as well as to provide a sealed connection between infusion catheter 3 and occlusion catheter 2. In some embodiments, the rotating capability of the collar 16 can allow for disengagement of occlusion catheter 2 from the infusion catheter 3 without causing movement and possible misalignment of the infusion catheter 3 within the native artery or graft.

Infusion Catheter

Referring to FIG. 1, the outer infusion catheter 3 has a nylon (or other suitable material) tubular body. In one embodiment, the catheter 3 is of a 3 French inner diameter and 4, 5, 6, or 7 French outer diameter having a central lumen 17 that is continuous from the proximal 18 to the distal 9 end of the catheter 3.

In one embodiment, the tubular shaft portion of the catheter 3 includes an infusion zone 10 with a plurality of slits $S_n$ (wherein n is an integer greater than 0) that serve as pressure responsive valves, e.g. as described in U.S. Pat. Nos. 5,205,034 and 5,267,979, which are herein incorporated by reference in their entirety. For example, in some embodiments, the infusion zone has $S_n$, wherein n is 1, 2, 3, 4, 5, 6, 7, 8, 9, 10, 20, 30, 40, or more. The pressure responsive slits $S_n$ permit fluid to exit from the catheter lumen 17 in response to a pressure level created by introduction of fluid into the lumen by a syringe. In other embodiments, the outer infusion catheter 3 comprises a plurality of side holes rather than pressure responsive slits. In some embodiments, the infusion catheter is a UNIFUSE™ catheter (Angiodynamics, Queensbury, N.Y.) (e.g., 4F UNI*FUSE™ infusion catheter) or similar device.

As shown in FIG. 1, the infusion zone 10 of the infusion catheter 3 is defined as the shaft portion between the optional distal infusion zone marker $M_{distal}$ and the optional proximal infusion zone marker $M_{proximal}$. Thrombolytic agent injected through the straight through port 20 into the annular space defined by lumen 17 will exit from the slits $S_n$ on the shaft portion between the two optional markers $M_{distal}$ and $M_{proximal}$. In one embodiment, marker $M_{proximal}$ is positioned about 1 cm proximal to the proximal most pressure responsive slit $S_n$ and marker $M_{distal}$ is positioned on the catheter 3 about 1 cm or so distal to the distal most pressure responsive slit $S_n$. The infusion catheter 3 optionally may also have one or more additional markers to assist the operator in accurately positioning the infusion zone 10 within the graft. For example, in one embodiment, the optional positioning marker can be positioned on the catheter 3 shaft proximal to infusion zone marker $M_{proximal}$. Optional positioning marker can provide another visual indication of location and depth of the infusion zone 10 segment of the catheter 3, thus ensuring that lytic agent, e.g., is not infused into a non-target area outside of the graft. In some embodiments, markers (e.g., $M_{distal}$, $M_{proximal}$) are each optional.

As depicted in FIG. 2, the catheter 2 fits within infusion catheter 3 and is sealably connected to the catheter hub 14 by engaging a side port 22 of hub connector assembly 13. In the preferred embodiment, the infusion catheter 3 has a 3 French inner diameter and 4, 5, 6, or 7 French outer diameter. For example, in some embodiments, the annular passageway for fluid flow can be created between a three French occlusion catheter (e.g., a balloon catheter) and a 4, 5, 6, or 7 French infusion catheter when assembled together. The dimensions of the annular space are sufficient to allow the desired fluid flow into the treatment zone (e.g., the clot).

In other embodiments, the catheter 2 also performs the function of occluding the infusion catheter's opening at end 9 when fully inserted into the catheter lumen 17. The catheter 2 and catheter 3 components can be dimensioned such that the catheter 2 fits snugly within and occludes the opening at end 9. In one embodiment, the outer diameter of the balloon catheter 2 and the opening at end 9 of the outer infusion catheter 3 are both approximately 0.040" thus providing occlusion of the opening at end 9. In another embodiment, the lumen 17 of the infusion catheter 3 is approximately 0.048" in diameter transitioning down to a 0.040" diameter at the infusion catheter tip at end 9. Thus, in some embodiments, a separate occlusion element such as an occlusion ball or wire is not required with the current invention.

Fluid can be infused through a hub into the annular fluid passageway between the outer wall of the occlusion catheter 2 and the inner wall of infusion catheter 3. For example, a syringe (not shown) containing a thrombolytic agent can be connected to the straight through port 20. When injected through the straight through port 20, the fluid advances through the annular fluid passageway defined by lumen 17 and exits through the side port slits $S_n$ of the infusion catheter 3 into the vessel, graft, and/or clot therein. Because the inner diameter of the infusion catheter 3 is typically larger than the outer diameter of occlusion catheter 2, there is sufficient space within the infusion catheter for the passage of a liquid out of the infusion holes.

Preferably, the system components are dimensioned such that the infusion zone 10 is maximized and the device length outside the patient is minimized. In one embodiment, the infusion zone 10 length corresponds to the subject's overall treatment zone (e.g., clot mass) length in order to ensure uniform agent (e.g., thrombolytic agent) delivery throughout the treatment zone.

Sheath

In still further embodiments, the coaxial infusion catheter system 1 comprises: a) the occlusion catheter 2 component; b) the infusion catheter 3 component; and (c) a sheath 24 component.

Figure 3:
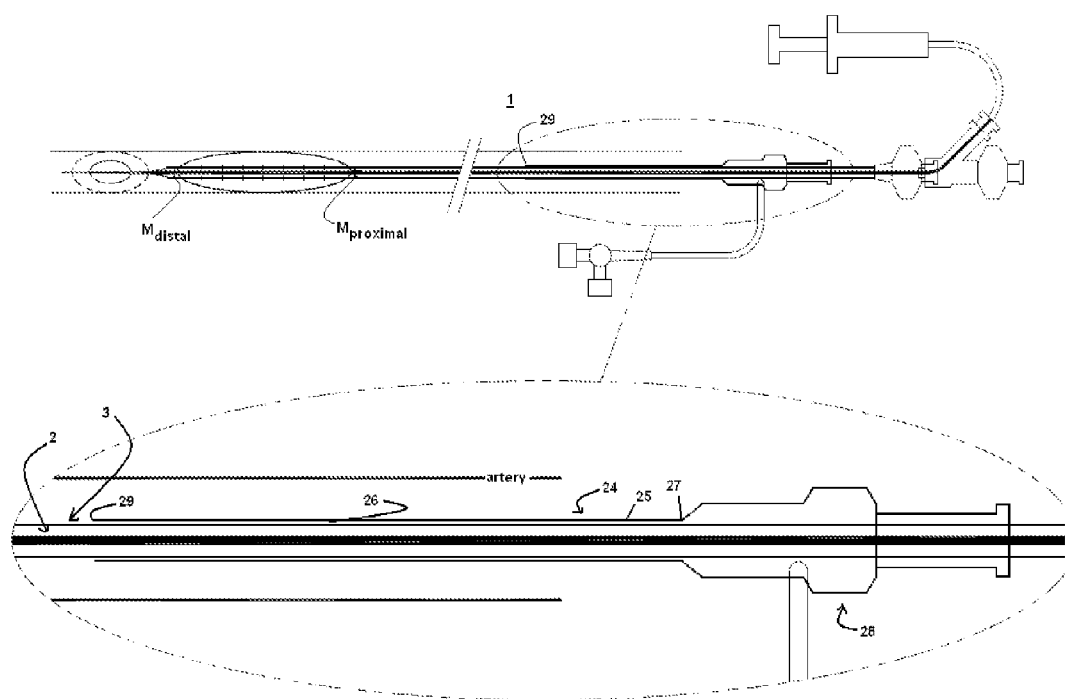
FIG. 3 is another schematic side view of the catheter system of FIG. 1.

Referring to FIG. 3, the sheath 24 comprises a tubular shaft 25 defining a central lumen 26. The sheath can be made of nylon or other similar material. The sheath further comprises an open proximal end 27, preferably fixedly secured to a hub 28, and a free open and unobstructed distal end 29. Preferably, in order to accommodate the infusion catheter, the sheath 24 has an inner diameter of at least 4, 5, 6, or 7 French with the central lumen 26 that is continuous from proximal end 27 to the open distal tip end 29 thus providing a direct path from the hub 28 to the inside of a vessel. In one embodiment, in the assembled state, optional markers $M_{distal}$ and $M_{proximal}$ of the infusion catheter extend beyond the sheath distal tip 29. In some embodiments, the sheath 24 has a length that is at least about 10 cm, illustratively, about 10 cm to about 90 cm.

Figure 4:
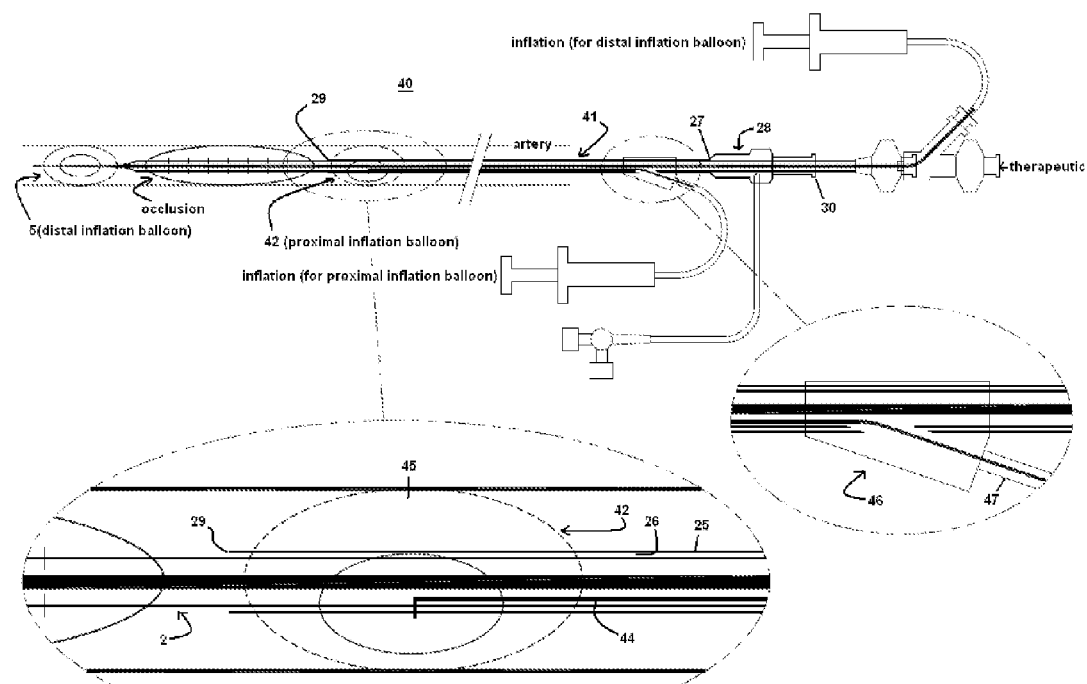
FIG. 4 is a schematic side view of another embodiment of a catheter system and its components in accordance with the present invention. A vessel or graft is occluded both proximal and distal to an occlusion (e.g., a clot).

In other aspects, the present invention is based on a coaxial infusion catheter system 40 depicted in FIG. 4. In one embodiment, the system 40 comprises (a) the occlusion catheter 2 component; (b) the infusion catheter 3 component; and (c) a sheath 41 comprising an occlusion chamber 42, wherein the occlusion chamber 42 is preferably disposed about the outer surface of tubular sheath shaft 25 about the distal region of shaft 25. The sheath 41 component of system 40 can provide for occlusion of a vessel or graft proximal to a treatment zone (e.g., proximal to a clot in an artery).

In one embodiment, the tubular sheath shaft 25 of FIG. 4 defines central lumen 26. The sheath further comprises open proximal end 27, preferably fixedly secured to hub 28, and a free open and unobstructed distal end 29. Preferably, sheath 41 has an inner diameter of at least 4, 5, 6, or 7 French with the central lumen 26 that is continuous from hub proximal end 30 to the open distal tip end 29 thus providing a direct path from the hub 28 to the inside of a vessel. In one embodiment, in the assembled state, optional markers $M_{distal}$ and $M_{proximal}$ of the infusion catheter 3 extends beyond the sheath 41 distal tip 29. In some embodiments, the sheath 41 has a length that is at least about 10 cm, illustratively, about 10 cm to about 90 cm.

In one embodiment, the inflatable occlusion chamber 42 is formed of a urethane polymer or a thermoplastic rubber elastomer. In other embodiments, the chamber 42 is an inflatable balloon. In another embodiment, the chamber 42 is a Latex balloon. The inflatable occlusion chamber 42 is expandable between a collapsed configuration and an inflated configuration. Upon inflation, the occlusion chamber occludes the vessel or graft by conforming to the shape of the space between the outer wall of the sheath shaft 25 and the inner wall of the vessel or graft in which the system 40 is disposed, such as a blood vessel. The occlusion chamber 42 can be sized as appropriate to substantially or completely occlude a particular vasculature in which the system will be used.

In one embodiment, the inflatable occlusion chamber 42 can be inflated to various sizes, depending on the volume of the material (e.g., air, gas, fluid) inserted into the inflatable occlusion chamber 42. In order to facilitate inflation to a desired size and avoid over-inflation, a chart can be provided listing various chamber sizes and the volume of inflation material generally required to achieve each size. In other embodiments, the inflatable occlusion chamber 42 expands to a pre-determined maximum size.

The inflatable occlusion chamber 42 can be inflated via inflation lumen 44, which is in communication with the interior of the inflatable occlusion chamber 42. When an inflation material (e.g., air, gas, fluid) is inserted through the inflation lumen 44 into the inflatable occlusion chamber 42, at least the intermediate portion 45 of chamber 42 moves radially outward.

In some embodiments, an inflation lumen 44 is disposed longitudinally along the inner wall of the sheath shaft 25 and is in communication with the occlusion chamber 42 disposed about the outer surface of the sheath shaft 25 about the distal region 43.

In one embodiment, the proximal end 27 of the sheath 41 is sealingly secured to a sheath hub 28. In the illustrated embodiment, sheath 41 also is provided with a side port structure 46 to provide a secured sealed fluid communication between an inflation source 47 and the interior of the inflation lumen 44. Side port structure 46 can be used to inject a suitable material (e.g., air, fluid) to inflate the occlusion chamber 42 thereby providing occlusion of a vessel proximal to infusion zone 10.

Thus, in other embodiments, system 40 can provide for occlusion of a vessel or graft at a position proximal to and/or distal to a treatment zone. Fluid can be infused into an annular fluid passageway between the outer wall of the occlusion catheter 2 and the inner wall of infusion catheter 3. For example, a syringe containing a thrombolytic agent can be used to inject a solution comprising the agent whereby the solution advances through the annular fluid passageway exiting through side port slits of the infusion catheter 3 into a vessel (e.g., artery), graft, and/or occlusion (e.g., thrombus). The inflatable occlusion chamber 5 of the occlusion catheter 2 can be inflated before, after, or along with injection of the thrombolytic agent, preferably before injection of the thrombolytic agent, to provide occlusion of the vessel or graft distal to the treatment zone. And, the inflatable occlusion chamber 42 of the sheath 41 can be inflated before, after, or along with injection of the thrombolytic agent, preferably before injection of the thrombolytic agent, to provide occlusion of the vessel or graft proximal to the treatment zone.

In other aspects, the present invention provides a sheath having an occlusion chamber for occluding a vessel, graft, and/or clot proximal to the treatment zone. The sheath, when employed at least in conjunction with an infusion catheter slideably inserted therein, is capable of providing for occlusion of a vessel or graft proximal to a treatment zone (e.g., proximal to a clot in an artery). In some embodiments, the sheath is sheath 41.

Figure 5:
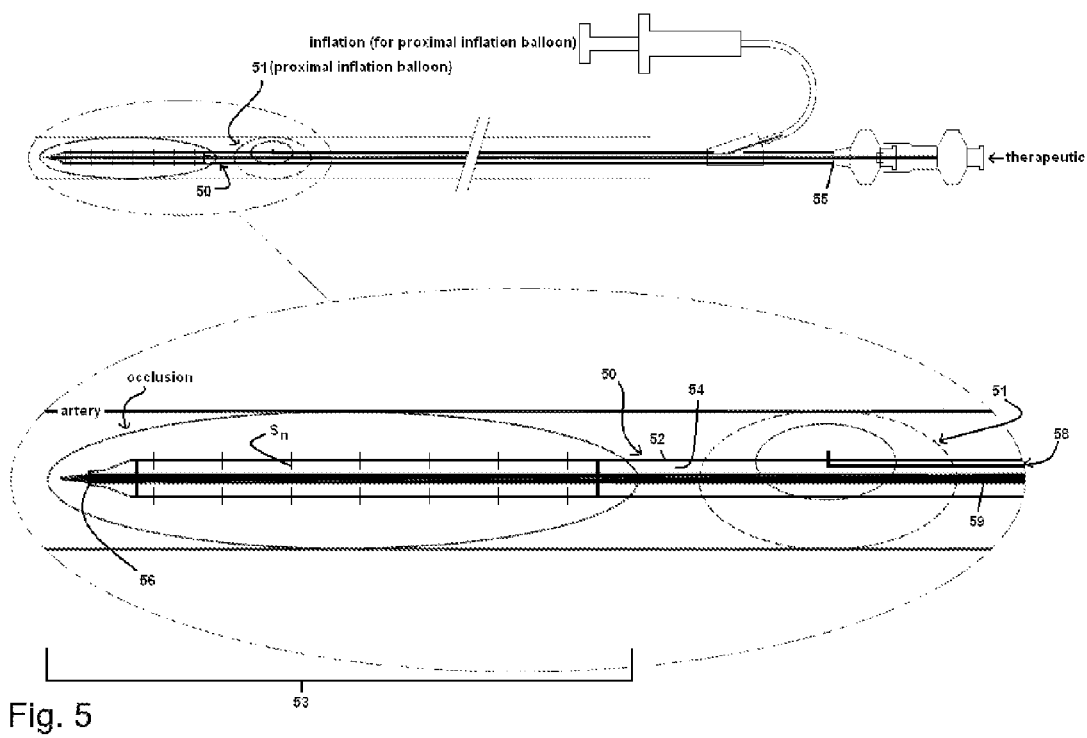
FIG. 5 is a schematic side view of one embodiment of a catheter system and its components in accordance with the present invention. A vessel or graft is occluded proximal to an occlusion (e.g., a clot).

In another aspect, the present invention is based on an infusion catheter 50 depicted in FIG. 5. The infusion catheter 50 comprises an occlusion chamber 51 disposed about the outer surface of the catheter shaft 52 about a region proximal to infusion zone 53.

In some embodiments, the infusion catheter 50 has a nylon (or other suitable material) tubular body. In one embodiment, the catheter 50 is of 4, 5, 6, or 7 French diameter with a central lumen 54 that is continuous from the proximal 55 to the distal 56 end of the catheter 50.

In one embodiment, the tubular shaft portion of the catheter 50 includes an infusion zone 53 with a plurality of slits $S_n$ that serve as pressure responsive valves. For example, in some embodiments, the infusion zone has $S_n$, wherein n is 1, 2, 3, 4, 5, 6, 7, 8, 9, 10, 20, 30, 40, or more. The pressure responsive slits $S_n$ permit fluid to exit from the catheter lumen 54 in response to a pressure level created by introduction of fluid into the lumen. Alternatively, infusion catheter 50 may include a plurality of side holes rather than pressure responsive slits.

The device is dimensioned such that the infusion zone is maximized and the device length outside the patient is minimized. Specifically, the infusion zone 53 length preferably corresponds to the patient's overall treatment zone (e.g., clot mass length) in order to ensure uniform drug delivery throughout the treatment zone. The portion of the device external to the patient is kept as short as possible to avoid complications arising from patient movement during lyse time. In other embodiments, the infusion catheter 50 may also have one or more markers to assist the operator in accurately positioning the infusion zone 53. For example, in one embodiment, one or more markers are positioned on the catheter shaft 52 about 1 cm proximal, distal, or both, to infusion zone 53.

In some embodiments, an occlusion lumen 58 is disposed longitudinally along the inner wall of the infusion catheter shaft 52 and is in communication with occlusion chamber 51 disposed at the outer surface of the catheter shaft 52 proximal to the infusion zone 53. In the illustrated embodiment, the occlusion lumen 58 corresponds to an inflation lumen in communication with the occlusion member 51, wherein the occlusion chamber 51 is an inflatable balloon.

In some embodiments, a separate occlusion element such as an occluding wire or ball is used to occlude the opening at end 56.

In one embodiment, occlusion of the distal opening of the catheter assembly may be accomplished by inserting an occluding wire 59 through a valve (e.g., a hemostasis valve coupled to a proximal end of the catheter which substantially prevents fluid from flowing out a proximal end of the catheter assembly during use), then inserting the wire further along the length of the catheter to or beyond the distal end 56.

The occluding wire can be configured to substantially seal the distal end 56 of the infusion catheter 50 during use in order to facilitate spray distribution through the holes. In some embodiments, the occluding wire comprises a wire body portion and a distal sealing ball portion. The sealing ball portion can form a substantially liquid-tight seal at the distal end of the catheter, thereby forcing liquid located proximal to the seal out of the infusion slits or holes of the catheter. Because the inner diameter of the catheter is typically larger than the diameter of the wire body portion of the occluding wire, there is ample space within the infusion catheter for the passage of a liquid out of the infusion holes.

In other embodiments, the inner diameter of the catheter 50 is reduced to a narrow neck at the distal end of the catheter. The sealing ball portion of the occluding wire can seat against the inner, narrow neck wall portion of the catheter when inserted into the distal end and thereby substantially occludes the distal opening of the catheter. Consequently, substantially any liquid forced through the catheter is caused to exit through the infusion holes rather than through the opening.

In another embodiment, the inner diameter of catheter 50 is constant throughout the catheter, but the diameter of the occluding ball is configured to substantially match the inner diameter of the catheter. Thus, the occluding ball can be slid to the distal tip, thereby substantially occluding the passageway of the catheter and forcing fluid to flow out of the side perfusion holes or slits proximal to the occluding ball.

In still further embodiments, a hub coupled to a proximal end of the elongate wire body of the occluding wire can be provided. The hub of the occluding wire can be configured to be coupled to the catheter 50. The hub of the occluding wire thus prevents the occluding tip from moving in a longitudinal direction with respect to the catheter once the occluding tip has been placed in a desired position with respect to the catheter 50.

Figure 6:
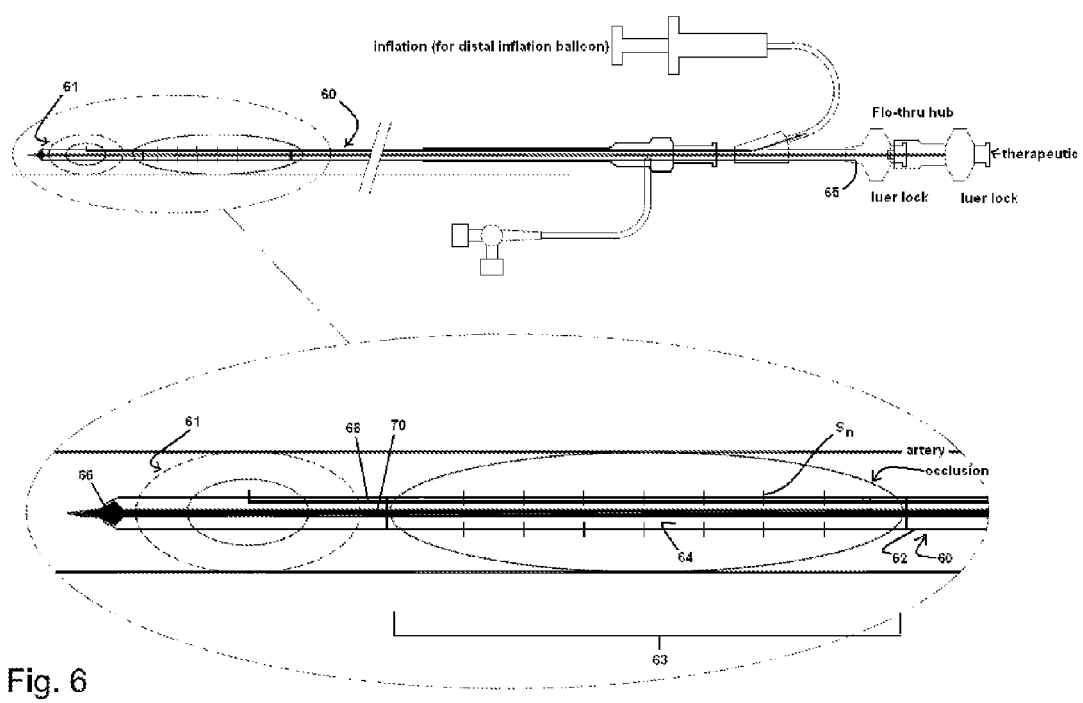
FIG. 6 is a schematic side view of another embodiment of a catheter system and its components in accordance with the present invention. A vessel or graft is occluded distal to an occlusion (e.g., a clot).

In another aspect, the present invention is based on an infusion catheter 60 depicted in FIG. 6. The infusion catheter 60 comprises an occlusion chamber 61 disposed about the outer surface of the catheter shaft 62 about a region distal to infusion zone 63.

In some embodiments, the infusion catheter 60 has a nylon (or other suitable material) tubular body. In one embodiment, the catheter 60 is of 4, 5, 6, or 7 French outer diameter with a central lumen 64 that is continuous from the proximal 65 to the distal 66 end of the catheter 60. In one embodiment, the tubular shaft portion of the catheter 60 includes an infusion zone 63 with a plurality of slits $S_n$ that serve as pressure responsive valves. For example, in some embodiments, the infusion zone has $S_n$, wherein n is 1, 2, 3, 4, 5, 6, 7, 8, 9, 10, 20, 30, 40, or more. The pressure responsive slits $S_n$ permit fluid to exit from the catheter lumen 64 in response to a pressure level created by introduction of fluid into the lumen. Alternatively, infusion catheter 60 may include a plurality of side holes rather than pressure responsive slits.

The device is dimensioned such that the infusion zone is maximized and the device length outside the patient is minimized. Specifically, the infusion zone 63 length preferably corresponds to the patient's overall treatment zone (e.g., clot mass length) in order to ensure uniform drug delivery throughout the treatment zone. The portion of the device external to the patient is kept as short as possible to avoid complications arising from patient movement during lyse time. In other embodiments, the infusion catheter 60 may also have one or more markers to assist the operator in accurately positioning the infusion zone 63. For example, in one embodiment, one or more markers are positioned on the catheter shaft 62 about 1 cm proximal, distal, or both, to infusion zone 63.

In some embodiments, an occlusion lumen 68 is disposed longitudinally along the inner wall of the infusion catheter shaft 62 and is in communication with occlusion chamber 61 disposed at the outer surface of the catheter shaft 62 proximal to the infusion zone 63. In the illustrated embodiment, the occlusion lumen 68 corresponds to an inflation lumen in communication with the occlusion member 61, wherein the occlusion chamber 61 is an inflatable balloon.

In some embodiments, a separate occlusion element such as an occluding wire or ball is used to occlude opening at end 66.

In one embodiment, occlusion of the distal opening of the catheter assembly may be accomplished by inserting an occluding wire 70 through a valve (e.g., a hemostasis valve coupled to a proximal end of the catheter which substantially prevents fluid from flowing out a proximal end of the catheter assembly during use), then inserting the wire further along the length of the catheter to or beyond the distal end 66.

The occluding wire can be configured to substantially seal the distal end 66 of the infusion catheter 60 during use in order to facilitate spray distribution through the holes. In some embodiments, the occluding wire comprises a wire body portion and a distal sealing ball portion. The sealing ball portion can form a substantially liquid-tight seal at the distal end of the catheter, thereby forcing liquid located proximal to the seal out of the infusion slits or holes of the catheter. Because the inner diameter of the catheter is typically larger than the diameter of the wire body portion of the occluding wire, there is ample space within the infusion catheter for the passage of a liquid out of the infusion holes.

In other embodiments, the inner diameter of the catheter 60 is reduced to a narrow neck at the distal end of the catheter. The sealing ball portion of the occluding wire can seat against the inner, narrow neck wall portion of the catheter when inserted into the distal end and thereby substantially occludes the distal opening of the catheter. Consequently, substantially any liquid forced through the catheter is caused to exit through the infusion holes rather than through the opening.

In another embodiment, the inner diameter of catheter 60 is constant throughout the catheter, but the diameter of the occluding ball is configured to substantially match the inner diameter of the catheter. Thus, the occluding ball can be slid to the distal tip, thereby substantially occluding the passageway of the catheter and forcing fluid to flow out of the side perfusion holes or slits proximal to the occluding ball.

In still further embodiments, a hub coupled to a proximal end of the elongate wire body of the occluding wire can be provided. The hub of the occluding wire can be configured to be coupled to the catheter 60. The hub of the occluding wire thus prevents the occluding tip from moving in a longitudinal direction with respect to the catheter once the occluding tip has been placed in a desired position with respect to the catheter 60.

Figure 7:
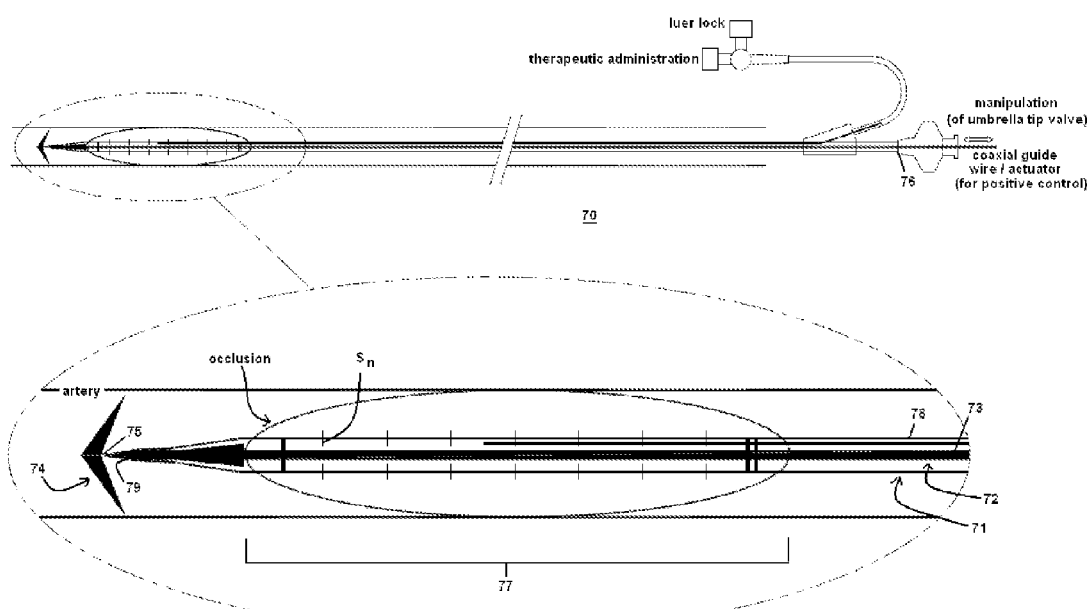
FIG. 7 is a schematic side view of one embodiment of a catheter system and its components in accordance with the present invention. An expandable occluding element coupled to a distal end of an elongate wire body provides for occluding a vessel or graft distal to an occlusion (e.g., a clot).

In one aspect, the present invention is based on a coaxial infusion catheter system 70 depicted in FIG. 7.

In one embodiment, the system comprises: (a) an infusion catheter 71 component; and (b) an occluding catheter 72 component having an elongate body 73, wherein an expandable occluding element 74 is coupled to a distal end 75 of the elongate body 73.

In some embodiments, the infusion catheter 71 has a nylon (or other suitable material) tubular body. In one embodiment, the catheter 71 is of 4, 5, 6, or 7 French outer diameter with a central lumen that is continuous from the proximal 76 to the distal 79 end of the infusion catheter 71. In some embodiments, the infusion catheter is a UNIFUSE™ catheter (Angiodynamics, Queensbury, N.Y.) (e.g., 4F UNI*FUSE™ infusion catheter) or similar device.

In one embodiment, the tubular shaft portion of the infusion catheter 71 includes an infusion zone 77 with a plurality of slits $S_n$ that serve as pressure responsive valves. For example, in some embodiments, the infusion zone has $S_n$, wherein n is 1, 2, 3, 4, 5, 6, 7, 8, 9, 10, 20, 30, 40, or more. The pressure responsive slits $S_n$ permit fluid to exit from the catheter lumen in response to a pressure level created by introduction of fluid into the lumen. Alternatively, infusion catheter 71 may include a plurality of side holes rather than pressure responsive slits.

The device is dimensioned such that the infusion zone is maximized and the device length outside the patient is minimized. Specifically, the infusion zone 77 length preferably corresponds to the patient's overall treatment zone (e.g., clot mass length) in order to ensure uniform drug delivery throughout the treatment zone. The portion of the device external to the patient is kept as short as possible to avoid complications arising from patient movement during lyse time. In other embodiments, the infusion catheter 71 may also have one or more markers to assist the operator in accurately positioning the infusion zone 77. For example, in one embodiment, one or more markers are positioned on the catheter shaft 78 about 1 cm proximal, distal, or both, to infusion zone 77.

Occluding Catheter

In some embodiments, the inner diameter of the infusion catheter 71 is larger than the diameter of the body 73 portion of the occluding catheter 72, therefore, there is ample space within the infusion catheter for the passage of a liquid out of the infusion holes as well as through infusion catheter at end 79.

In one embodiment, the expandable occluding element 74, when used in an open configuration in the expanded position, functions as a filter to filter blood; and, wherein element 74, when used in a closed configuration in the expanded position, functions to occlude the lumen of a vessel or graft at a position distal to end hole 79. Accordingly, in some embodiments, when the expandable occluding element 74 is in the closed configuration, system 70 can provide for completely blocking the lumen of a vessel or graft in order to increase the saturation of the thrombolytic agent into a clot during treatment, wherein when the expandable occluding element 74 is in the open configuration, blood flow can occur following the treatment in order to allow blood flow to be restored (e.g., restored in the leg) while also trapping emboli, if present.

Figure 8:
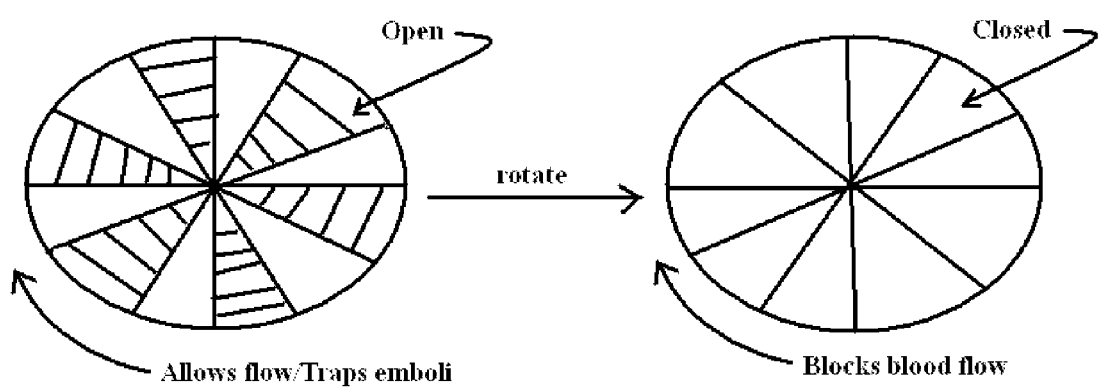
FIG. 8 is a plan view of the expandable occluding element of FIG. 7 illustrated in the open (blood flow) and closed (no blood flow) configuration.

Referring to FIG. 8, in one embodiment, the expandable occluding element 74 is configured as a dischargeable umbrella comprising two overlapping components with staggered shutters or overlapping slits. Depending on the degree of rotation, rotation of one of the components over the other allows for blood flow (the open configuration) or vessel/graft lumen occlusion (the closed configuration).

In some embodiments, the expandable occluding element can be configured to have an inherent tension that converts the element from a collapsed to an expanded/unfolded state, or it can be expanded/unfolded using a folding system. For example, the folding system can comprise a plurality of folding arms roughly similar to a typical umbrella.

In other embodiments, the expandable occluding element is a dischargeable umbrella comprising a mesh or net material for trapping emboli. Suitable mesh include those known in the art. For example, polyurethane meshes may be used, such as Saati and Tetko meshes. These are available in sheet form and can be easily cut and formed into a desired shape. Preferably, the mesh is capable of entrapping embolic material without unduly disrupting blood flow when the system is employed with the expandable occluding element in the open configuration.

In some embodiments, the mesh can trap material that is at least about 5 micrometers, illustratively, at least about: 5, 10, 15, 20, 25, 30, 35, 40, 50, 60, 70, 80, 90, and 100 micrometers.

In one embodiment, the occluding catheter 72 can be inserted through a valve (e.g., a hemostasis valve coupled to a proximal end of the catheter which substantially prevents fluid from flowing out a proximal end of the catheter assembly during use), then inserting the occluding catheter 72 further along the length of infusion catheter 71 through the end hole 79.

In other aspects, a kit is provided which comprises the systems and/or one or more of the devices/components of the present invention. In some embodiments, the kit further comprises a therapeutic, for example a thrombolytic agent such as plasmin, etc.

What is claimed is:

1. A method for treating thrombosis in a vessel or graft comprising:
   (a) inserting a coaxial occlusion/infusion catheter system into a subject's vessel or graft and advancing the catheter to a position where a distal tip of the catheter system lies distal to a thrombus, the thrombus length corresponding to the infusion zone;
   wherein the coaxial occlusion/infusion catheter system comprises:
      (i) an occlusion catheter component having an occlusion chamber, wherein the occlusion catheter component provides for occlusion of the vessel or graft distal to the infusion zone;
      (ii) an infusion catheter component comprising 1 to 40 pressure responsive slits or side holes and one or more detectable markers for positioning all of said pressure responsive slits or side holes within the thrombus, wherein at least a portion of the occlusion catheter component is coaxially positioned within the infusion catheter component; and
      (iii) an outer sheath component having an occlusion chamber, wherein at least a portion of the infusion catheter is coaxially positioned within the outer sheath component, wherein the sheath component provides for the occlusion of the vessel or graft proximal to the infusion zone;
   wherein a composition comprising plasmin can be administered by infusion into an annular fluid passageway between an outer wall of the occlusion catheter and an inner wall of the infusion catheter, wherein said composition comprising plasmin exits said pressure responsive slits or side holes thereby providing the composition comprising plasmin within the thrombus;
   (b) activating the occlusion chamber of the occlusion catheter prior to the administering step, thereby occluding the vessel or graft distal to the infusion zone, wherein the occlusion chamber of the occlusion catheter is activated by inflation through an inflation lumen that is in contact with the occlusion chamber of the occlusion catheter with a suitable volume of material comprising air, gas, or fluid;
   (c) activating the occlusion chamber of the sheath prior to the administering step thereby occluding the vessel or graft proximal to the infusion zone, wherein the occlusion chamber of the sheath is activated by inflation through an inflation lumen that is in contact with the occlusion chamber of the sheath with a suitable volume of material comprising air, gas, or fluid;
   (d) administering the composition comprising plasmin into the infusion zone; and
   (e) incubating the composition comprising plasmin in the infusion zone, thereby dissolving the thrombus.

2. The method of claim 1, further comprising:
   (f) inactivating the occlusion chamber of the occlusion catheter component and inactivating the occlusion chamber of the sheath component, thereby permitting normal blood flow through the vessel or graft; and
   (g) removing the catheter system from the subject's vessel or graft.

3. The method of claim 1, wherein the occlusion catheter distal tip extends beyond the infusion catheter's distal tip such that the occlusion chamber lies distal to the infusion catheter's distal tip and thereby is capable of occluding a vessel or graft distal to the infusion zone wherein the distal tip of the infusion catheter lies.

4. The method of claim 1, wherein the infusion zone is maximized.

5. The method of claim 1, wherein the thrombus is a peripheral arterial occlusion.

6. A method for treating thrombosis in a vessel or graft comprising:
   (a) inserting a coaxial occlusion/infusion catheter system into a subject's vessel or graft and advancing the catheter to a position where a distal tip of the catheter system lies distal to a thrombus, the thrombus length corresponding to the infusion zone;
   wherein the coaxial occlusion/infusion catheter system comprises:
      (i) an occlusion catheter component having an occlusion chamber, wherein the occlusion catheter component provides for occlusion of the vessel or graft distal to the infusion zone;
      (ii) an infusion catheter component, comprising 1 to 40 pressure responsive slits or side holes and one or more detectable markers for positioning all of said pressure responsive slits or side holes within the thrombus, wherein at least a portion of the occlusion catheter component is coaxially positioned within the infusion catheter component; and
      (iii) an outer sheath component wherein at least a portion of the infusion catheter is coaxially positioned within the outer sheath component;

wherein a composition comprising plasmin can be administered by infusion into an annular fluid passageway between an outer wall of the occlusion catheter and an inner wall of the infusion catheter, wherein said composition comprising plasmin exits said pressure responsive slits or side holes thereby providing the composition comprising plasmin zone within the thrombus;

(b) activating the occlusion chamber of the occlusion catheter prior to the administering step, thereby occluding the vessel or graft distal to the infusion zone, wherein the occlusion chamber of the occlusion catheter is activated by inflation through an inflation lumen that is in contact with the occlusion chamber of the occlusion catheter with a suitable volume of material comprising air, gas, or fluid;

(c) administering the composition comprising plasmin into the infusion zone; and (d) incubating the composition comprising plasmin in the infusion zone, thereby dissolving the thrombus.

7. The method of claim 6, further comprising:

(e) inactivating the occlusion chamber of the occlusion catheter component thereby permitting normal blood flow through the vessel or graft; and (f) removing the catheter system from the subject's vessel or graft.

8. The method of claim 6, wherein the occlusion catheter distal tip extends beyond the infusion catheter's distal tip such that the occlusion lies distal to the infusion catheter's distal tip and thereby is capable of occluding a vessel or graft distal to the infusion zone wherein the distal tip of the catheter lies.

9. The method of claim 6, wherein the infusion zone is maximized.

10. The method of claim 6, wherein the thrombus is a peripheral arterial occlusion.

11. A method for treating thrombosis in a vessel or graft comprising:

(a) inserting a coaxial occlusion/infusion catheter system into a subject's vessel or graft and advancing the catheter to a position where a distal tip of the catheter system lies distal to a thrombus, the thrombus length corresponding to the infusion zone;

wherein the infusion catheter system comprises:
  (i) an occlusion wire component; and
  (ii) an infusion catheter component comprising 1 to 40 pressure responsive slits or side holes and one or more detectable markers for positioning all of said pressure responsive slits or side holes within the thrombus and having an occlusion chamber, wherein at least a portion of the occlusion wire component is coaxially positioned within the infusion catheter component,
wherein the infusion catheter component provides for occlusion of the vessel or graft distal to the infusion zone; and
wherein a composition comprising plasmin can be administered by infusion into the infusion catheter, wherein said composition comprising plasmin exits said pressure responsive slits or side holes thereby providing the composition comprising plasmin within the thrombus;

(b) activating the occlusion chamber of the inclusion catheter prior to the administering step, thereby occluding the vessel or graft distal to the infusion zone;
wherein the occlusion chamber of the infusion catheter is activated by inflation through an inflation lumen that is in contact with occlusion chamber of the infusion catheter with a suitable volume of material comprising air, gas, or fluid;

(c) administering the composition comprising plasmin into the infusion zone; and (d) incubating the composition comprising plasmin in the infusion zone, thereby dissolving the thrombus.

12. The method of claim 11, further comprising:

(e) inactivating the occlusion chamber of the inclusion catheter component and, thereby permitting normal blood flow through the vessel or graft; and (f) removing the catheter system from the subject's vessel or graft.

13. The method of claim 11, wherein the infusion zone corresponds to a subject's treatment zone comprising the thrombus mass length within the vessel or graft.

14. The method of claim 11, wherein the infusion zone is maximized.

15. The method of claim 11, wherein the thrombus is a peripheral arterial occlusion.

* * * * *